(12) United States Patent
Vivero Sánchez et al.

(10) Patent No.: US 11,020,455 B2
(45) Date of Patent: Jun. 1, 2021

(54) COLONY STIMULATING FACTOR FOR USE IN PANCREATIC OR COLON CANCER TREATMENT

(71) Applicant: ENDOR TECHNOLOGIES, S.L., Barcelona (ES)

(72) Inventors: Laura Vivero Sánchez, Barcelona (ES); Luciano Sobrevals Amieva, Barcelona (ES); Rafael Miñana Prieto, Cervelló (ES); Judith Sendra Cuadal, Barcelona (ES); Joaquín Querol Sastre, Barcelona (ES)

(73) Assignee: ENDOR TECHNOLOGIES, S.L, Barcelona (ES)

( * ) Notice: Subject to any disclaimer, the term of this patent is extended or adjusted under 35 U.S.C. 154(b) by 593 days.

(21) Appl. No.: 15/747,408

(22) PCT Filed: Jul. 28, 2016

(86) PCT No.: PCT/EP2016/068007
§ 371 (c)(1),
(2) Date: Jan. 24, 2018

(87) PCT Pub. No.: WO2017/017187
PCT Pub. Date: Feb. 2, 2017

(65) Prior Publication Data
US 2018/0214517 A1 Aug. 2, 2018

(30) Foreign Application Priority Data

Jul. 30, 2015 (EP) .................................. 15179043

(51) Int. Cl.
| | | |
|---|---|---|
| *A61K 38/19* | (2006.01) | |
| *A61K 45/06* | (2006.01) | |
| *A61K 31/519* | (2006.01) | |
| *A61K 31/337* | (2006.01) | |
| *A61K 31/4745* | (2006.01) | |
| *A61K 31/436* | (2006.01) | |
| *A61K 31/517* | (2006.01) | |
| *A61K 31/555* | (2006.01) | |
| *A61K 31/7068* | (2006.01) | |
| *A61K 31/404* | (2006.01) | |
| *A61P 35/00* | (2006.01) | |
| *A61K 9/00* | (2006.01) | |

(52) U.S. Cl.
CPC .......... *A61K 38/193* (2013.01); *A61K 9/0019* (2013.01); *A61K 31/337* (2013.01); *A61K 31/404* (2013.01); *A61K 31/436* (2013.01); *A61K 31/4745* (2013.01); *A61K 31/517* (2013.01); *A61K 31/519* (2013.01); *A61K 31/555* (2013.01); *A61K 31/7068* (2013.01); *A61K 45/06* (2013.01); *A61P 35/00* (2018.01)

(58) Field of Classification Search
None
See application file for complete search history.

(56) References Cited

U.S. PATENT DOCUMENTS

| | | | | |
|---|---|---|---|---|
| 2006/0008448 A1* | 1/2006 | Xu | ........................ | C12N 15/113 424/93.2 |
| 2010/0227818 A1* | 9/2010 | Bock | .................... | A61K 38/385 424/85.1 |
| 2010/0303714 A1* | 12/2010 | Kirn | ........................ | C12N 15/86 424/1.11 |
| 2013/0078279 A1 | 3/2013 | Nemunaitis et al. | | |
| 2013/0266553 A1* | 10/2013 | Ballance | ................ | C07K 14/56 424/94.6 |
| 2014/0227179 A1 | 8/2014 | Liu et al. | | |
| 2015/0202268 A1 | 7/2015 | Bock et al. | | |

FOREIGN PATENT DOCUMENTS

| | | |
|---|---|---|
| EP | 2612676 A1 | 7/2013 |
| WO | WO 88/06452 A1 | 9/1988 |
| WO | WO 2008/122415 A1 | 10/2008 |

OTHER PUBLICATIONS

International Search Report and Written Opinion dated Nov. 30, 2016 for PCT/EP2016/068007, 17 pages.
Attia, Mohammed A., et al: "Immmunology of spontaneous mammary carcinomas in mice. V. Acquired tumor resistance and enhancement in strain A mice infected with mammary tumor virus", Cancer Research Aug. 1966, vol. 26, Part 1, pp. 1787-1800.
Carson, E.J., et.al. "Phase II trial of sargramostim (yeast-derived recombinant human GM-CSF) as monotherapy for advanced sarcomas", 2000 American Society of Clinical Oncology, Proceedings of ASCO, vol. 19, Abstract 2219.
Demirci, Umut, et.al: "Serum granulocyte macrophage-colony stimulating factor: a tumor marker in colorectal carcinoma?", Asian Pacific Journal of Cancer Prevention 2009, vol. 10, pp. 1021-1024.
DiMasi, Joseph A., et al: "Economics of new oncology drug development", Journal of Clinical Oncology, Jan. 10, 2007, vol. 25, No. 2, pp. 209-216.
Fujiwara, Yushi, et.al: "Granulocyte colony-stimulating factor-producing ascending colon cancer as indicated by histopathological findings: report of a case", Osaka City Med. J. 2011, vol. 57, No. 2, pp. 79-84.

(Continued)

*Primary Examiner* — Gary B Nickol
*Assistant Examiner* — Jegatheesan Seharaseyon
(74) *Attorney, Agent, or Firm* — Squire Patton Boggs (US) LLP

(57) ABSTRACT

There is provided a Colony Stimulating Factor (CSF) as an active ingredient for use in the treatment of colon or pancreatic cancer through an increase in neutrophilia, wherein the Colony Stimulating Factor is selected from the group consisting of Granulocyte Macrophage Colony Stimulating Factor (GM-CSF) and Granulocyte Colony Stimulating Factor (G-CSF). The new use for these two recombinant proteins represents a new treatment option for two of the most frequent forms of cancer.

17 Claims, 8 Drawing Sheets

(56) References Cited

OTHER PUBLICATIONS

Groblewska, Magdalena, et. al: "Serum levels of granulocyte colony-stimulating factor (G-CSF) and macrophage colony-stimulating factor (M-CSF) in pancreatic cancer patients", Clin. Chem. Lab. Med. 2007, vol. 45, No. 1, pp. 30-34.

Jaganjac, Morana, et. al: "The involvement of granulocytes in spontaneous regression of Walker 256 carcinoma", Cancer Letters 260, 2008, vol. 260, pp. 180-186.

Joshita, Satoru, et.al: "Granulocyte-colony stimulating factor-producing pancreatic adenosquamous carcinoma showing aggressive clinical course", Internal Medicine, Jan. 25, 2009, vol. 48, pp. 687-691.

Kaufman, Howard L., et. al: "Current status of granulocyte-macroiphage colony-stimulating factor in the immunotherapy of melanoma", May 13, 2014, Journal for Immunotherapy of cancer, Biomed Central LTD London UK. vol. 2, No. 1, p. 11.

Kim, Joong Sun, et. al: "Administration of granulocyte colony-stimulating factor with radiotherapy promotes tumor growth by stimulating vascularization in tumor-bearing mice", Oncology Reports, Apr. 14, 2015, vol. 34, pp. 147-154.

Morris, K.T., et. al: "G-CSF and G-CSFR are highly expressed in human gastric and colon cancers and promote carcinoma cell proliferation and migration", British Journal of Cancer, Jan. 21, 2014, vol. 110, pp. 1211-1120.

Mroczko, Barbara, et. al: "Serum macrophage-colony stimulating factor levels in 15 colorectal cancer patients correlate with lymph node metastasis and por prognosis", Clinica Chimica Acta 380, Feb. 27, 2007, vol. 380, pp. 208-212.

"Neutropenia in cancer patients: risk factors and management", Mar. 1, 2010 Retrieved from the Internet: URL: http//www.cancerworld.org/pdf [retrieved on Oct. 8, 2015].

Rini, Brian L., et. Al: "Clinical and Immunological characteristics of patients with serologic progression of prostate cander achieving long-term disease control with granulocyte-macrophage colony-stimulating factor", Jun. 2006 Journal of Urology, vol. 175, No. 6, pp. 2087-2091.

Spitler, Lynn E., et. Al: "Adjuvant therapy of stage III and IV malignant melanoma using granulocyte-macrophage colony-stimulating factor", Apr. 2000 Journal of Clinical Oncology, American Society of Clinical Onclolgy vol. 18, No. 14, pp. 1614-1621.

* cited by examiner

COLONY STIMULATING FACTOR FOR USE IN PANCREATIC OR COLON CANCER TREATMENT

The present invention provides granulocyte-colony stimulating factor and granulocyte macrophage-colony stimulating factor for use in the therapy of two of the most widespread forms of malignancies, namely pancreatic and colon cancer. The use of these two recombinant proteins represents a new therapeutic option to treat these two diseases in the clinic.

BACKGROUND ART

Cancer is one of the leading causes of death in the first world. Contrary to what was perceived in the past, cancer is now taken as an umbrella term encompassing a huge diversity of conditions caused by a myriad of variables, among which genetic, infective and lifestyle associated factors stand out. Because there is a huge number and diversity of pathological processes that can lead to the development of a malignancy, it is now widely recognized that each type of cancer responds favorably to certain therapeutic treatments but not to others. Remarkably, even the same type of cancer can have different therapeutic responses in different patients, depending on the detailed pattern of cancer-causing mutations featured. Even more remarkably, cells from the same tumor derived from the same patient can also respond differently to disease modifying treatments depending on their clonal origin.

In spite of all biomedical advances and the efforts undertaken by society, public institutions and the pharmaceutical and biotech industries to tackle this disease, many malignancies still have a huge mortality rate. The war on cancer is far from being won. The heterogeneous character of this disease impairs the development of universal treatments, and so specific treatments for the different forms must be devised and developed. Currently, it is estimated that the total cost involved in developing a new cancer biological therapy is on the order of 1.2 billion dollars (DiMasi J A, Grabowski H G. "Economics of new oncology drug development" J. Clin. Oncol. 2007, vol. 25, pp. 209-216). However, in spite of the great advances accomplished in the last decades, most of the treatments in use carry a heavy burden as the therapeutic molecules are in most cases not selective for the cancerous cell, and so a range of toxic side effects always ensue.

Neutropenia, which is an abnormally low neutrophil count, is among the most serious and frequent chemotherapy-related side effects. Most cancer therapies are cytotoxic, impairing cancerous cell division by a range of molecular mechanisms. This leads to cancer cells not being able to divide as quickly, which reverts to a therapeutic benefit. However, the rate of division for many normal cell lines which divide with high frequency in the body (such as epithelial cells or white blood cells) is also impaired by the non-selective treatments, which leads to serious side effects. Neutrophils usually represent the biggest percentage of circulating white blood cells, and serve as the primary defense against infections by destroying bacteria found in the blood. Therefore, cancer patients with chemotherapy-related neutropenia are more susceptible to bacterial infections and, without prompt medical attention, these conditions can become life-threatening and deadly.

To compensate for the depletion of neutrophils due to cytotoxic chemotherapy, cancer patients following a chemotherapy regimen are concomitantly treated with a range of neutrophil enhancing therapies. The current standard treatment for neutropenia caused by chemotherapy is based on the use of two recombinant proteins, namely Granulocyte Macrophage Colony Stimulating Factor (GM-CSF) and Granulocyte Colony Stimulating Factor (G-CSF). They both stimulate the survival, proliferation, differentiation, and function of neutrophil precursors and mature neutrophils, thus compensating the neutrophil depleting properties of anti-tumor therapy and avoiding unwanted infections. A range of analogs of G-CSF and GM-CSF have been approved for the treatment of chemotherapy-related neutropenia, such as Filgrastim, Pegfilgrastim, Lenograstim, Sargramostim and Molgramostim.

In the light of the high development costs cited above, the pharmaceutical industry is searching for innovative formulas to reduce the overall waste of resources due to attrition. In this respect, one of the current trends in order to find new therapies with contained cost is what has been termed as drug repurposing or reprofiling. This strategy is based on finding new indications for already developed drugs. Because approved drugs have been taken through preclinical and clinical phases, their ADME properties, bioavailabilities and toxicities are known to be acceptable, and therefore most of the barriers associated to these hurdles are, in principle, not an issue. Therefore, if a known safe drug is found a second indication, different from the one for which it was developed, it follows that its development should be much easier than that of a freshly discovered molecule for which no experimental in vivo or human tests are available.

The reprofiling strategy can be used for any given drug, whether it is a small organic molecule or a recombinant protein. Among the proteins tested for repurposing in the cancer field, GM-CSF and G-CSF deserve a special mention. They have been tested as chemotherapies in a range of cancers with varying degrees of success. GM-CSF has been proven to have a therapeutic effect when administered subcutaneously as a long-term therapy in melanoma patients after surgical resection (Spitler L E., et. al. "Adjuvant therapy of stage III and IV malignant melanoma using granylocyte-macrophage colony-simulating factor" J. Clin. Oncol. 2000, vol. 18, pp. 1614-1621). Also, it has been proven to have a therapeutic benefit in patients with prostate cancer (Rini B I, et. al. "Clinical and immunological characteristics of patients with serologic progression of prostate cancer achieving long-term disease control with granulocyte-macrophage colony-stimulating factor" J. Urol. 2006, vol. 175, pp. 2087-2091). However, in other types of malignancies, results have been disappointing. For instance, the use of GM-CSF as a monotherapy in the treatment of sarcoma did not reveal a therapeutic benefit (Carson E J., et. al. "Phase II trial of sargramostim (yeast-derived recombinant human GM-CSF) as monotherapy for advanced sarcomas" Proc. Am. Soc. Clin. Oncol. 2000, vol 18, Abstract 2219).

In the case of colon cancer, the role of GM-CSF and G-CSF seems to be detrimental as found in numerous references of the prior art. Thus, GM-CSF has been linked to disease progression in human colorectal cancer (Demirci, U., et. al. "Serum granulocyte macrophage-colony stimulating factor: a tumor marker in colorectal carcinoma?, Asian Pac. J. Cancer Prev. 2009, vol. 10, pp. 1021-1024; Mroczko B. "Serum macrophage-colony stimulating factor levels in colorectal cancer patients correlate with lymph node metastasis and poor prognosis" Clin. Chim. Acta. 2007, vol. 380, pp. 208-12. Likewise, G-CSF has also been linked to invasiveness and malignancy in colon cancer (Fujiwara Y. et. al. "Granulocyte colony-stimulating factor-producing ascending colon cancer as indicated by histopathological findings: report of a case." Osaka City Med. J. 2011, vol. 57, pp. 79-84; Kim J S. et. al. "Administration of granulocyte colony-stimulating factor with radiotherapy promotes tumor growth by stimulating vascularization in tumor-bearing mice". Oncol Rep. 2015 vol. 34, pp. 147-54; Morris K T. et. al. "G-CSF and G-CSFR are highly expressed in human gastric and colon cancers and promote carcinoma cell proliferation and migration" Br. J. Cancer 2014, vol. 110, pp. 1211-20. As for pancreatic cancer, the potential role of GM-CSF and G-CSF in the clinics still remains to be determined (Groblewska M. "Serum levels of granulocyte colony-stimulating factor (G-CSF) and macrophage colony-stimulating factor (M-CSF) in pancreatic cancer patients" Clin. Chem. Lab. Med. 2007, vol. 45, pp. 30-4; Joshita S. "Granulocyte-colony stimulating factor-producing pancreatic adenosquamous carcinoma showing aggressive clinical course" Intern. Med. 2009, vol. 48, pp. 687-91.

Because colon and pancreatic cancers are found in the top-10 in terms of incidence, accounting for a total of 694.000 and 330.000 deaths in 2012 respectively, and because they still have associated a poor prognosis in a significant percentage or cases, novel treatments for combating them are badly needed. It would be highly desirable to find new treatments for these two conditions among the current pharmacopeia.

SUMMARY OF THE INVENTION

Inventors have surprisingly found that exogenous G-CSF or GM-CSF, administered by injection as soluble active pharmaceutical ingredients, have a strong chemotherapeutic effect in colon and pancreatic cancer, that is, these two approved recombinant protein drugs are capable of slowing down the progression of cancerous cells in colon and pancreatic cancer. Remarkably, the potency is comparable to chemotherapeutic treatments currently in use such as gemcitabine.

The marked anti-tumor activity of G-CSF and GM-CSF for colon and pancreatic cancer, caused by the increased numbers of neutrophils, open up the way for repurposing these two recombinant drugs (currently in use for the treatment of neutropenia) as two new antineoplastic therapeutic options for these two forms of cancer.

It is found that the administration of either G-CSF or GM-CSF in order to induce neutrophilia in a patient, has a marked therapeutic effect for the two types of cancer claimed herein. Of note, this therapeutic effect is irrespective of whether the subject has a pharmacologically-induced neutropenia. The invention is based on inducing neutrophilia in the cancer patients independently of the fact that they may or may not have neutropenia caused by the treatment of their disease with any other drugs.

Thus, a first aspect of the present invention is a Colony Stimulating Factor (CSF) as an active ingredient for use in the treatment of colon or pancreatic cancer through an increase in neutrophilia, wherein the Colony Stimulating Factor is selected from the group consisting of Granulocyte Macrophage Colony Stimulating Factor (GM-CSF) and Granulocyte Colony Stimulating Factor (G-CSF)

Remarkably, inventors have proven with the experimental data found herein that G-CSF and GM-CSF are effective in a variety of colon and pancreatic cancer in vivo models, which underlines their versatility as therapeutic drugs for these two malignancies.

It is depicted the antitumoral efficacy of G-CSF in human pancreatic SC tumors. Athymic nu/nu mice bearing Panc-1 SC tumors were daily treated with subcutaneous G-CSF injection at a dose of 10 µg/Kg, while GE was injected intraperitoneal at a dose of 80 mg/Kg two times per week during the whole experiment. Total tumor volume (mm$^3$±SE) in saline (solid lines), G-CSF 10 µg/Kg (dashed lines) and GE 80 mg/kg (dotted) groups, for 48 days of treatment are represented.

Figure 2:
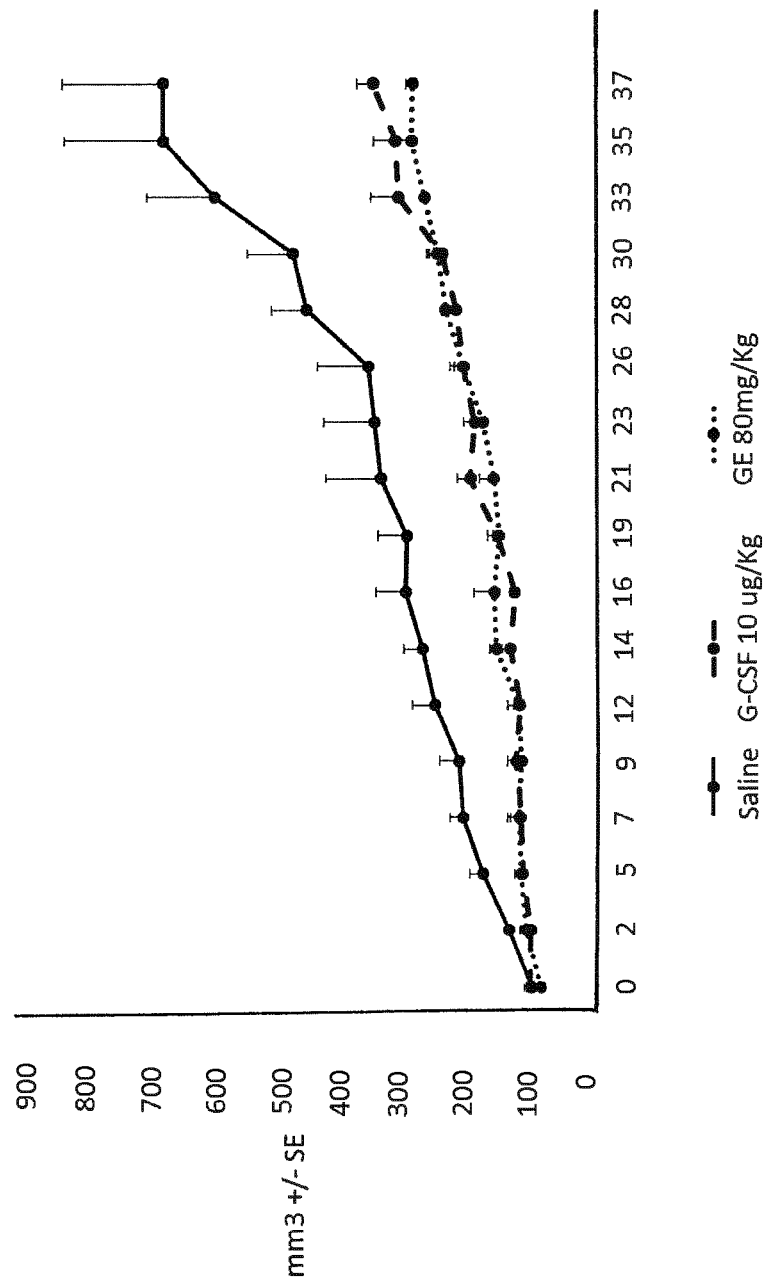

FIG. 2. G-CSF antitumoral efficacy in MiaPaca model.

It is depicted the antitumoral efficacy of G-CSF in human pancreatic SC tumors. Athymic nu/nu mice bearing MiaPaca SC tumors were daily treated with subcutaneous G-CSF injection at a dose of 10 µg/kg, while GE was injected intraperitoneal at a dose of 80 mg/Kg two times per week during the whole experiment. Total tumor volume (mm$^3$±SE) in saline (solid lines), G-CSF 10 µg/kg (dashed lines) and GE 80 mg/kg (dotted) groups, for 37 days of treatment are represented.

Figure 3:
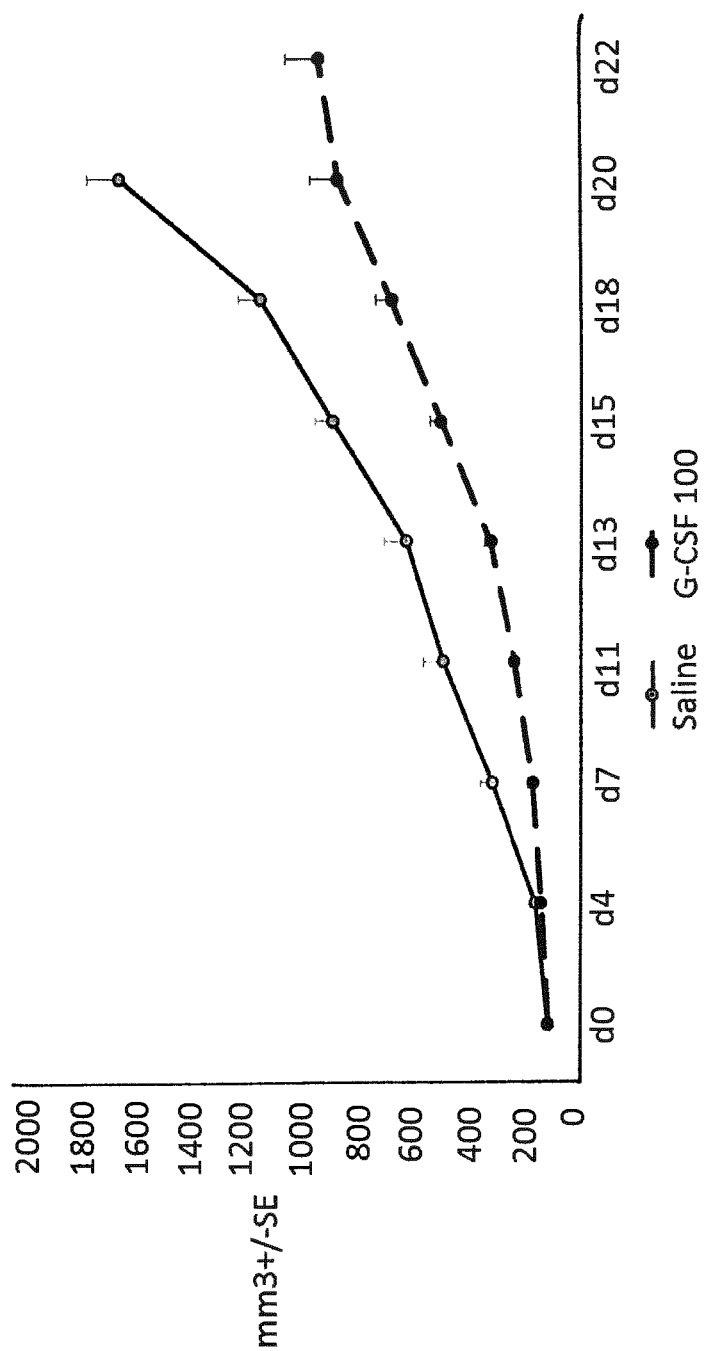

FIG. 3. G-CSF antitumoral efficacy in Panc02 model.

It is depicted the antitumoral efficacy of G-CSF in murine pancreatic SC tumors. C57BJL6 mice bearing Panc02 SC tumors were daily treated with subcutaneous G-CSF injection at a dose of 100 µg/kg. Total tumor volume (mm$^3$±SE) in saline (solid lines), G-CSF 100 µg/kg (dashed lines) groups, for 22 days of treatment are represented.

Figure 4:
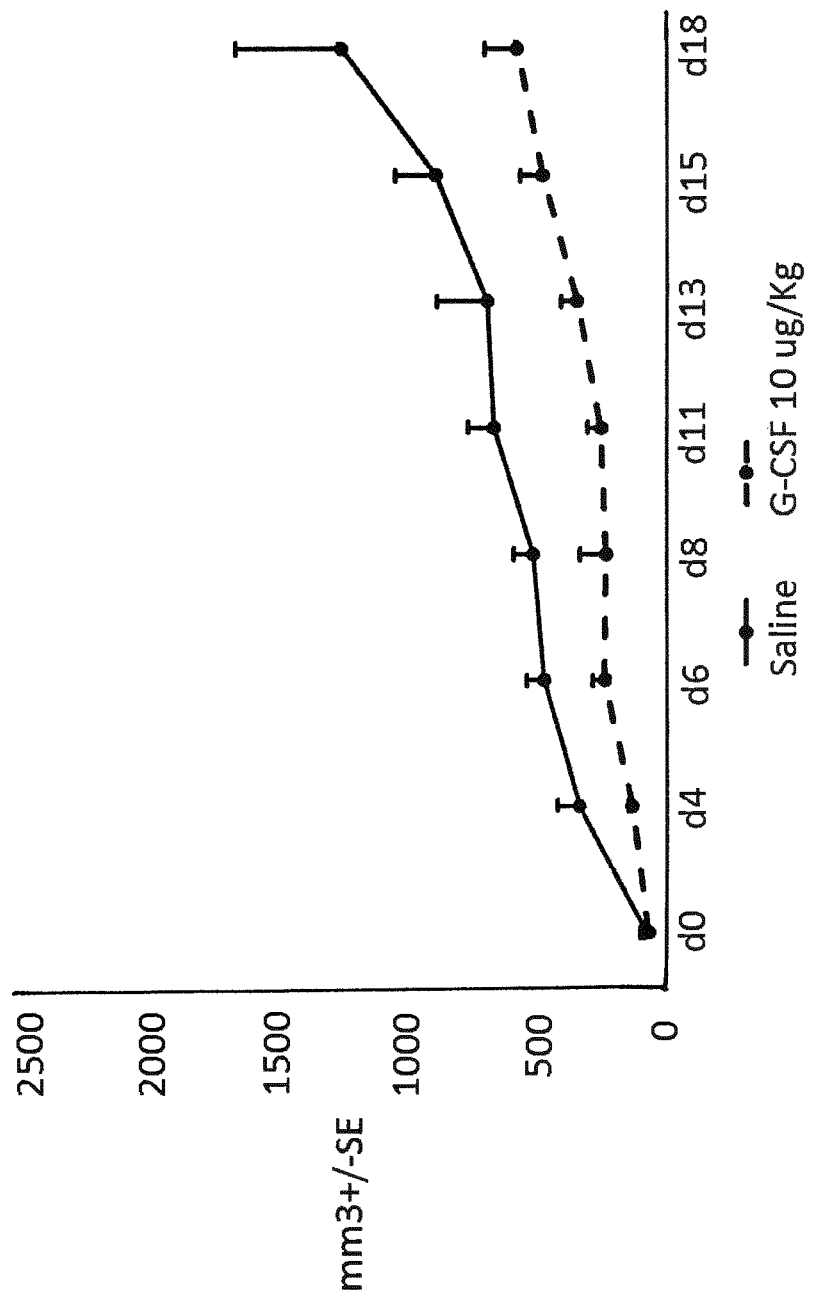

FIG. 4. G-CSF antitumoral efficacy in Colon-26 model.

It is depicted the antitumoral efficacy of G-CSF in mouse colorectal SC tumors. BalbC mice bearing colorectal SC tumors were daily treated with subcutaneous G-CSF injection at a dose of 10 µg/kg. Total tumor volume (mm$^3$±SE) in saline (solid lines) and G-CSF10 µg/kg (dashed lines) groups, for 18 days of treatment are represented.

Figure 5:
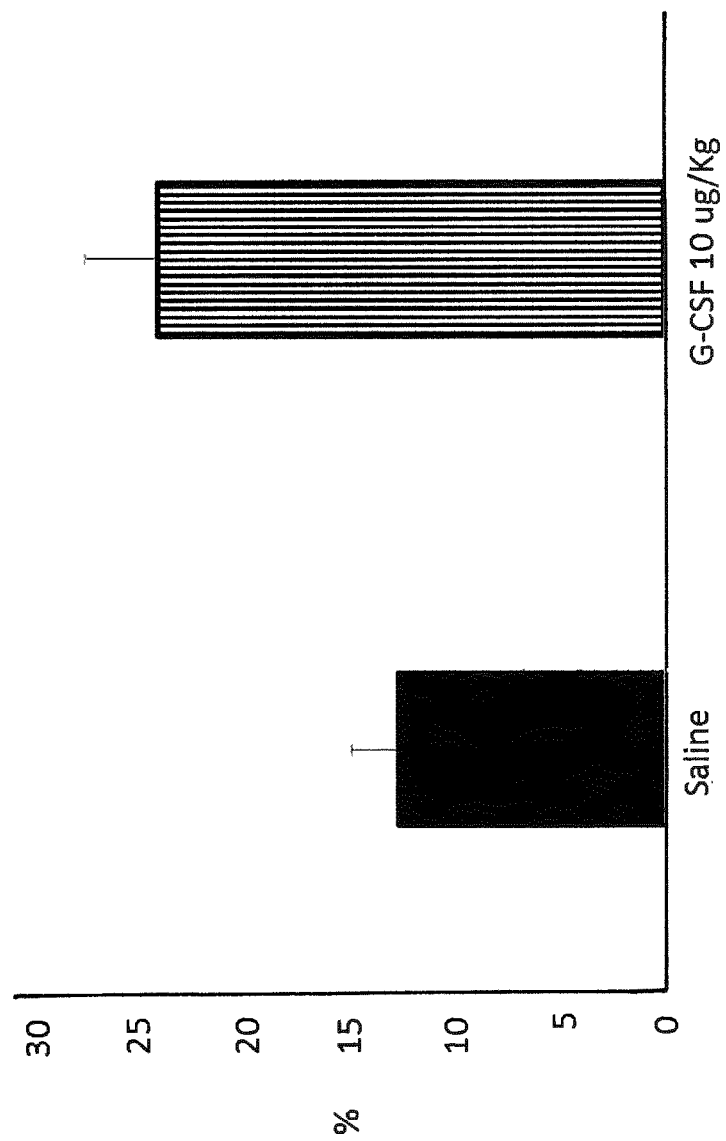

FIG. 5. Tumor granulocytes in Colon-26 model.

Depiction of the tumor granulocyte levels, defined as a CD45+CD11b+Ly6G+ triple positive population, analyzed by flow cytometry from Colon-26 tumors treated with 10 µg/kg of G-CSF during 5 days. Granulocytes cells from tumor are represented as a % of positive cells±SE.

Figure 6:
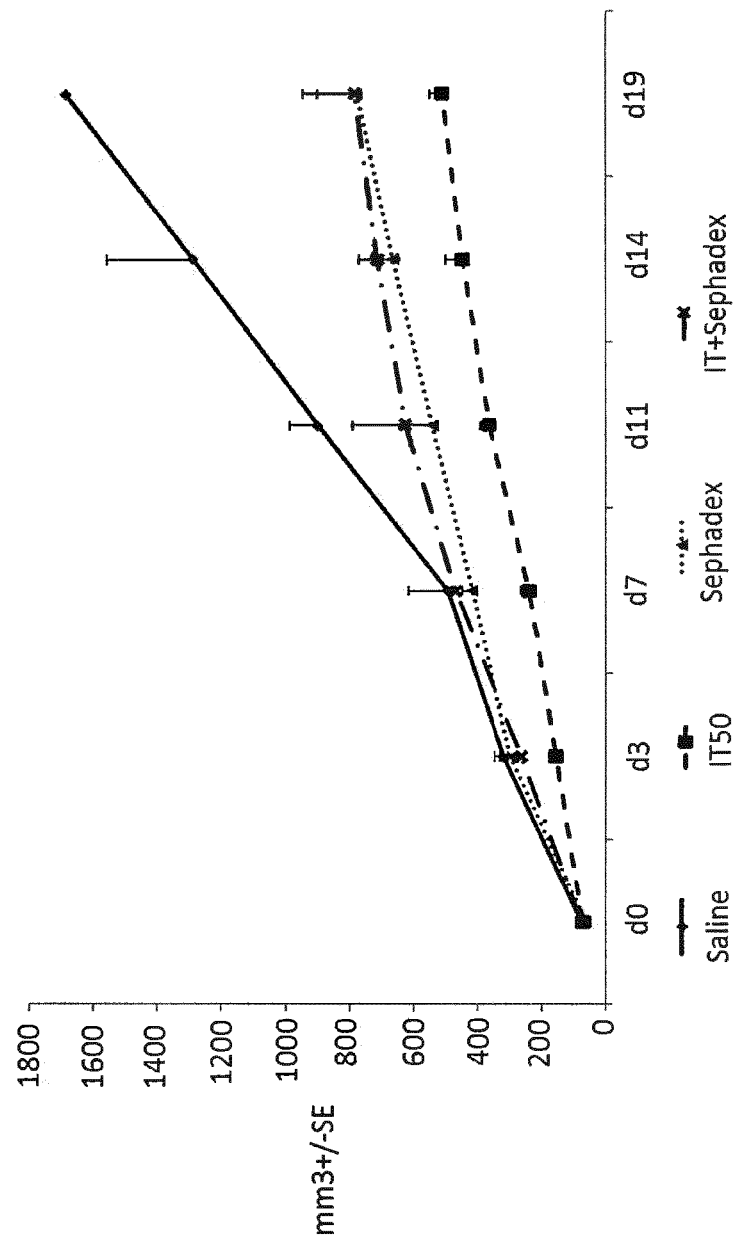

FIG. 6. Effect of Sephadex on G-CSF antitumoral efficacy in Colon-26 model.

Depiction of the antitumoral efficacy of G-CSF in colorectal SC tumors. BalbC mice bearing Colon-26 SC tumors, with and without Sephadex papula, were treated daily with subcutaneous G-CSF injection at a dose of 50 ug/kg. Total tumor volume (mm$^3$±SE) of saline (circle), G-CSF 50 µg/kg (square, abbreviated IT50), Sephadex-Saline (triangle), and Sephadex+G-CSF 50 µg/kg (cross, abbreviated IT-Sephadex.), for 19 days of treatment are represented.

Figure 7:
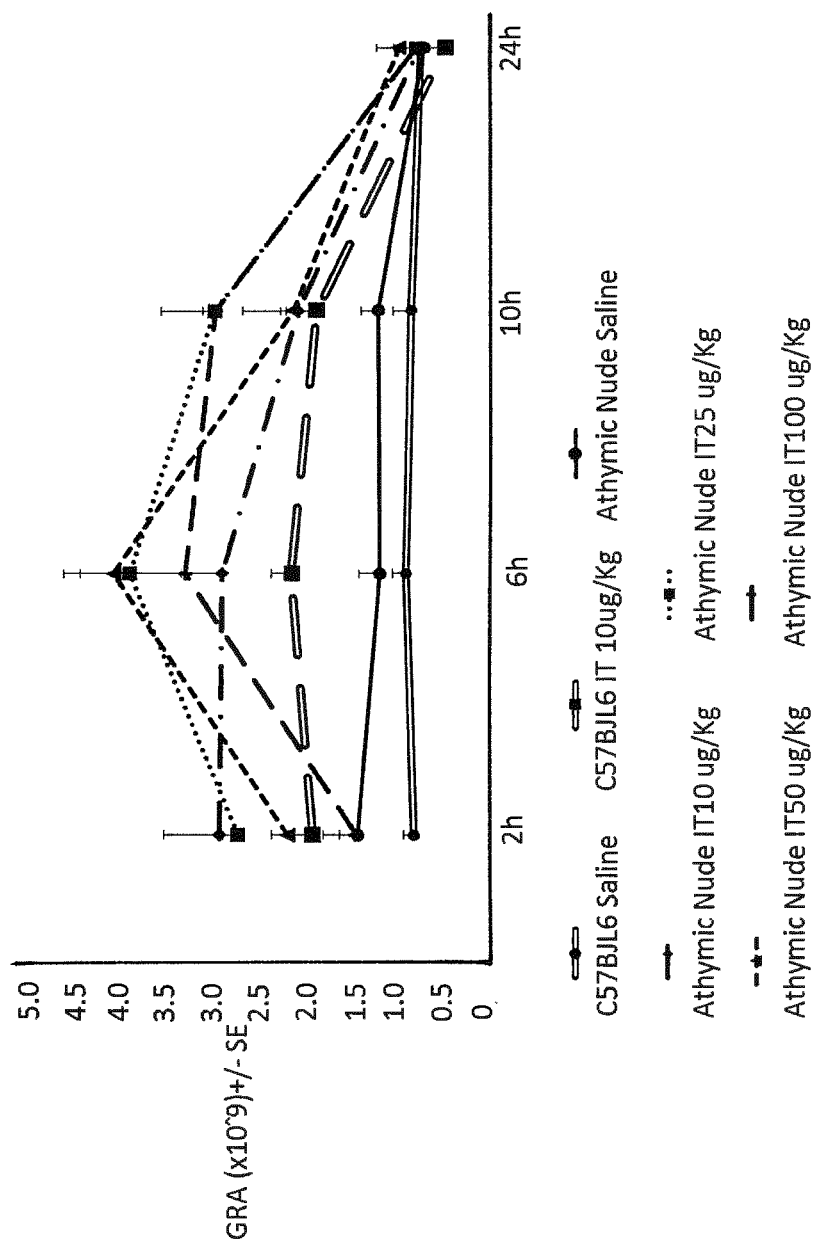

FIG. 7. Effect of G-CSF on peripheral blood granulocytes levels in healthy immunocompetent and immunodeficient mice.

Depiction of the peripheral blood granulocytes levels in healthy C57BJL6 and Athymic nu/nu mice after the subcutaneous injection of a single dose of G-CSF (10 µg/kg) in C57BJL6, and 10, 25, 50 and 100 µg/kg of G-CSF in Athymic nu/nu mice. Blood samples were taken at different time points and peripheral blood granulocytes levels are represented as a total number of granulocytes (GRAx10^9/L).

Figure 8:
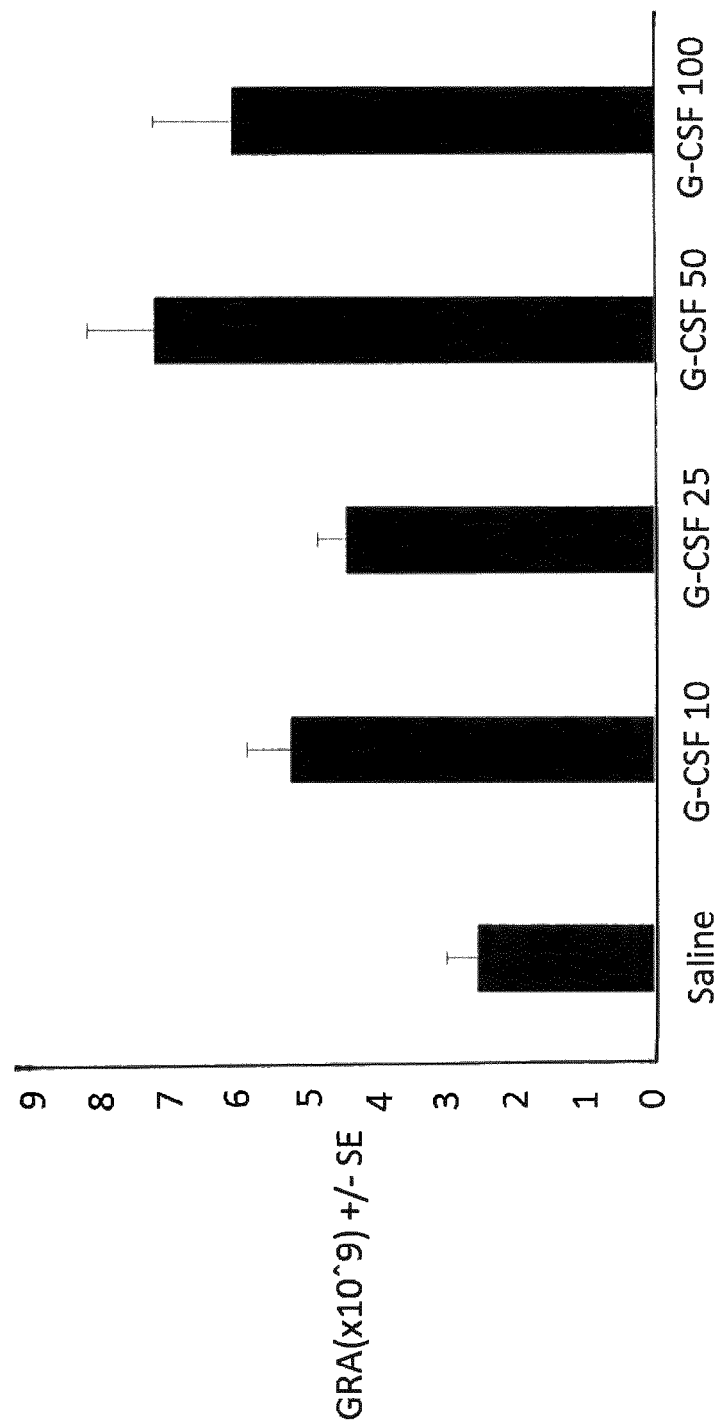

FIG. 8. Effect of G-CSF on peripheral blood granulocytes levels in MiaPaca model.

Depiction of peripheral blood granulocytes levels in Athymic nu/nu mice bearing MiaPaca SC tumors after the subcutaneous injection of G-CSF 10, 25, 50 and 100 µg/kg. Blood samples were taken at 1.5 hr and peripheral blood granulocytes levels are represented as a total number of granulocytes (GRA $10^9$/L).

DETAILED DESCRIPTION OF THE INVENTION

For the sake of understanding, the following definitions are included and expected to be applied throughout description, claims and drawings.

The term "antineoplastic therapy" as used herein, refers to a treatment that is based on administering an anti-cancer active pharmaceutical ingredient (API), that is, a treatment where the API is given with the purpose of directly or indirectly arresting, delaying or slowing down the uncontrolled cellular growth and division of cancerous cells.

The term "increase in neutrophilia" as related to the use in the treatment of colon or pancreatic cancer, refers to an antineoplastic therapy whose effects are basically driven by increasing the amounts of neutrophils.

The term "neutrophil" as used herein, refers to neutrophil granulocytes which are the most abundant (up to 75%) type of white blood cells in mammals and are a central part of the innate immune system. They derive from stem cells in the bone marrow. Together with basophils and eosinophils, they form part of the polymorphonuclear cell family (PMNs).

The term "Colony Stimulating Factor" (CSF) as used herein, refers to a series of glycoproteins that bind protein receptors on hemopoietic cells, triggering a variety of intracellular signaling events that ultimately lead to proliferation and differentiation of the different hemopoietic cell linages. The family is composed of Macrophage-Colony Stimulating Factor (M-CSF), GM-CSF and G-CSF. When in the present invention CSF is used (being any of G-CSF, M-CSF or GM-CSF), it relates to any of the wild-type mammal, particularly human glycoproteins, as well as to any active pharmaceutical ingredients that derive from these proteins and including amino acid modifications. These amino acid modifications comprise amino acid additions due to the recombinant technology-based production process of the proteins, pegylations and glycosylations.

The term "soluble Colony Stimulating Factor (CSF) protein" as used herein, refers to a CSF that is administered parenterally
in the form of an isolated soluble protein. This protein, when administered directly to the patient, is not conjugated covalently to any other macromolecule such as an antibody or any other therapeutic protein, nor is it administered in the form of a nucleic acid, vector or otherwise, coding for the soluble CSF protein.

The protein Granulocyte-Colony Stimulating Factor (G-CSF) also known as Colony Stimulating Factor 3 (CSF3) or C17orf33, is a four-helix bundle structured glycoprotein that stimulates the production of granulocytes by the bone marrow. It is a member of the cytokine family produced by endothelial cells and macrophages and controls the production, differentiation, and function of two related white blood cell populations, the granulocytes and the monocytes-macrophages. The human G-CSF protein can be found in the Uniprot database with the entry P09919 (version 169, last updated 29 Apr. 2015). There are currently several active pharmaceutical ingredients which are very similar to human G-CSF, namely Filgrastim, Lenograstim, Lipegfilgrastim and Pegfilgrastim. Filgrastim differs from the natural protein in that an N-terminal methionine residue has been added to allow for its expression in bacteria, as this product is produced in E. coli (and therefore is not glycosylated as it is when expressed by a eukaryote cell). Pegfilgrastim is the pegylated version of Filgrastim with increased half-life due to lower clearance. Both APIs are currently in standard use in the clinics for the treatment of chemotherapy-related neutropenia in cancer patients receiving chemotherapy.

The protein Granulocyte Macrophage-Colony Stimulating Factor (GM-CSF) also known as Colony Stimulating Factor 2 (CSF2), is a four-helix bundle structured glycoprotein that stimulates the production of granulocytes and macrophages by the bone marrow. It is a member of the cytokine family and controls the production, differentiation, and function of two related white blood cell populations, the granulocytes and the monocytes-macrophages. The human GM-CSF protein can be found in the Uniprot database with the entry P04141 (version 160, last updated 27 May 2015). There are currently two active pharmaceutical ingredients based on human GM-CSF, namely Sargramostim and Molgramostim. They are both prescribed for the treatment of chemotherapy-related neutropenia in cancer patients receiving chemotherapy.

The term "pancreatic cancer" as used herein refers both to exocrine and endocrine tumors.

The term "colon cancer" as used herein refers to any cancer that originates in the colon or rectum, especially adenocarcinoma, but also gastrointestinal stromal tumor (gist), squamous cell carcinoma, neuroendocrine and sarcoma of the colon The term "neutrophil-increasing antineoplastic therapy" as used herein, refers to an antineoplastic therapy whose effects are basically driven by increasing the amounts of neutrophils.

The term "inducing neutrophilia" as used herein refers to a treatment that is given to a subject or a patient with the goal of increasing his/her neutrophil count above standard levels and sustaining it in time, irrespective of the fact that he/she might have neutropenia induced by any previous or concomitant treatment. The treatment in a human subject would lead to neutrophil counts that might be increased by a percentage from 600% to 1000%. It should be mentioned that the neutrophil count in a human adult is considered to be normal when it is approximately between 2,000 u/microliter and 7,500 u/microliter. The "induced neutrophilia" could result in neutrophil counts that are between 20,000 u/microliter and 45,000 u/microliter, and therefore, counts that are clearly increased when compared to their standard values.

The term "therapeutically effective amount" as used herein, refers to the amount of the CSF that, when administered, is sufficient to have a therapeutic effect. The particular dose administered according to this invention will of course be determined by the particular circumstances surrounding the case, including the CSF administered, the exact route of administration, the particular cancer being treated, the recipient subject, and similar considerations.

As mentioned above, a first aspect of the present invention is a Colony Stimulating Factor (CSF) as an active ingredient for use in the treatment of colon or pancreatic cancer through an increase in neutrophilia, wherein the Colony Stimulating Factor is selected from the group consisting of Granulocyte Macrophage Colony Stimulating Factor (GM-CSF) and Granulocyte Colony Stimulating Factor (G-CSF).

The Colony Stimulating Factor (CSF) for use as a neutrophil-increasing antineoplastic therapy in the treatment of colon or pancreatic cancer, wherein the Colony Stimulating Factor is selected from the group consisting of Granulocyte Macrophage Colony Stimulating Factor (GM-CSF) and Granulocyte Colony Stimulating Factor (G-CSF) is considered also part of the invention.

The invention can be reformulated as the use of a Colony Stimulating Factor (CSF) in the manufacture of a medicament comprising as active ingredient a Colony Stimulating Factor selected from the group consisting of Granulocyte Macrophage Colony Stimulating Factor (GM-CSF) and Granulocyte Colony Stimulating Factor (G-CSF), for the treatment of colon or pancreatic cancer through an increase in neutrophilia.

The invention can also be reformulated as a method of treatment of colon or pancreatic cancer through an increase in neutrophilia which comprises administering a therapeutically effective amount of a Colony Stimulating Factor (CSF) as an active ingredient wherein the Colony Stimulating Factor is selected from the group consisting of Granulocyte Macrophage Colony Stimulating Factor (GM-CSF) and Granulocyte Colony Stimulating Factor (G-CSF), to a subject in need thereof, including a human.

In a particular embodiment of the first aspect of the invention, the Colony Stimulating Factor (CSF) is administered as the sole active ingredient.

In a particular embodiment of the first aspect of the invention, the Colony Stimulating Factor (CSF) is a soluble Colony Stimulating Factor protein.

In a particular embodiment of the first aspect of the invention, the administration of the Colony Stimulating Factor (CSF) is by injection.

In a particular embodiment of the first aspect of the invention, the use of the Colony Stimulating Factor is for inducing neutrophilia.

It also forms part of the invention, a Colony Stimulating Factor (CSF) for use as antineoplastic therapy in the treatment of colon or pancreatic cancer.

Additionally, it also forms part of the invention a Colony Stimulating Factor (CSF) for use as neutrophil-increasing antineoplastic therapy in the treatment of colon or pancreatic cancer.

In a particular embodiment of the first aspect of the invention, the neutrophilia is sustained for a period of time from 4 to 20 weeks.

In a particular embodiment of the first aspect of the invention, the neutrophilia is sustained for a period of time from 8 to 16 weeks.

In a particular embodiment of the first aspect of the invention, the soluble Colony Stimulating Factor (CSF) protein is for use in inducing neutrophilia.

In a particular embodiment of the first aspect of the invention, the colon cancer is adenocarcinoma of the colon.

In another particular embodiment of the first aspect of the invention, the pancreatic cancer is exocrine pancreatic cancer.

In another particular embodiment of the first aspect of the invention, the Colony Stimulating Factor is Granulocyte Macrophage Colony Stimulating Factor (GM-CSF).

In another particular embodiment of the first aspect of the invention, the Granulocyte Macrophage Colony Stimulating Factor (GM-CSF) is Sargramostim or Molgramostim.

In another particular embodiment of the first aspect of the invention, the GM-CSF is a mammal and particularly human recombinant GM-CSF.

In another particular embodiment of the first aspect of the invention, the Colony Stimulating Factor is Granulocyte Colony Stimulating Factor (G-CSF).

In another particular embodiment of the first aspect of the invention, the Granulocyte Colony Stimulating Factor (G-CSF) is Filgrastim, Pegfilgrastim, Lenograstim and Lipegfilgrastim.

In another particular embodiment of the first aspect of the invention, the G-CSF is a mammal and particularly human recombinant G-CSF.

In another particular embodiment of the first aspect of the invention, the Colony Stimulating Factor is administered at a dose of between 100 and 1000 µg/day In another particular embodiment of the first aspect of the invention, the Colony Stimulating Factor is administered at a dose of between 100 and 500 µg/day for G-CSF and at a dose of between 200-800 µg/day for GM-CSF.

In another particular embodiment of the first aspect of the invention, the Colony Stimulating Factor is administered at a dose of between 290 and 310 µg/day.

In another particular embodiment of the first aspect of the invention, the Colony Stimulating Factor is administered at a dose of 300 µg/day.

In another particular embodiment of the first aspect of the invention, the CSF is administered at a dose of 1-50 µg/kg/day.

In another particular embodiment of the first aspect of the invention, the CSF is administered at a dose of 5 µg/kg/day, 10 µg/kg/day, 15 µg/kg/day, 20 µg/kg/day, 25 µg/kg/day, 30 µg/kg/day, 35 µg/kg/day, 40 µg/kg/day, 45 µg/kg/day or 50 µg/kg/day.

In another particular embodiment of the first aspect of the invention, the Colony Stimulating Factor is administered over a period of between 6 and 16 weeks.

In another particular embodiment of the first aspect of the invention, the Colony Stimulating Factor is administered intermittently in a series of cycles, wherein the cycles can be from 1 to 5, each cycle of administration being interspersed with resting periods, wherein each resting period is from 1 to 12 weeks, and each cycle of administration is from 4 to 16 weeks.

In another particular embodiment of the first aspect of the invention, the Colony Stimulating Factor is administered over a period of 2.5 and 3.5 months.

In another particular embodiment of the first aspect of the invention, the Colony Stimulating Factor is administered over a period of 3 months.

In another particular embodiment of the first aspect of the invention, the Colony Stimulating Factor is administered subcutaneously, orally, intramuscularly or intravenously. This means that the administration route is selected from subcutaneous administration, oral administration, intramuscular administration and intravenous administration.

In another particular embodiment of the first aspect of the invention, the Colony Stimulating Factor is administered at a dose of between 100 and 500 µg/day for G-CSF and at a dose of between 200-800 µg/day for GM-CSF for a period of between 4 and 16 weeks, subcutaneously.

In another particular embodiment of the first aspect of the invention, the Colony Stimulating Factor is administered at a dose of between 1 and 50 µg/kg/day for a period of between 4 and 16 weeks, subcutaneously.

In another particular embodiment of the first aspect of the invention, the Colony Stimulating Factor is administered at a dose of 300 µg/day over a period of 3 months subcutaneously.

In another particular embodiment of the first aspect of the invention, the induced neutrophilia has a neutrophil count from 15,000 to 60,000 units/microliter.

In another particular embodiment of the first aspect of the invention, the induced neutrophilia has a neutrophil count from 15,000 to 50,000 units/microliter.

In another particular embodiment of the first aspect of the invention, the induced neutrophilia has a neutrophil count from 15,000 to 45,000 units/microliter.

In another particular embodiment of the first aspect of the invention, the induced neutrophilia has a neutrophil count from 20,000 to 40,000 units/microliter.

In another particular embodiment of the first aspect of the invention, the induced neutrophilia has a neutrophil count from 25,000 to 35,000 units/microliter.

In another particular embodiment of the first aspect of the invention, the Colony Stimulating Factor is administered as a sole chemical antineoplastic therapy, optionally I combination with radiotherapy.

In another particular embodiment of the first aspect of the invention, the Colony Stimulating Factor is administered as a combination chemical antineoplastic therapy.

In another particular embodiment of the first aspect of the invention, the Colony Stimulating Factor is administered simultaneously or sequentially with radiotherapy.

In another particular embodiment of the first aspect of the invention, the G-CSF or GM-CSF is administered separately, simultaneously or sequentially together with a compound selected from the group consisting of gemcitabine, paclitaxel, 5-fluorouracyl, leucovorin, irinotecan, oxaliplatin, erlotinib, everolimus, mitomycin C, sunitinib or any combination thereof, for the treatment of pancreatic cancer.

In another particular embodiment of the first aspect of the invention, the G-CSF or GM-CSF is administered separately, simultaneously or sequentially together with a compound selected from the group consisting of gemcitabine, paclitaxel, 5-fluorouracyl, leucovorin, irinotecan, oxaliplatin, erlotinib, everolimus, mitomycin C, sunitinib or any combination thereof, for the treatment of pancreatic cancer, and the administration of said compounds is optionally combined with radiotherapy.

In another particular embodiment of the first aspect of the invention, the G-CSF or GM-CSF is administered separately, simultaneously or sequentially together with a compound selected from the group consisting of 5-fluorouracyl, capecitabine, leucovorin, irinotecan, oxaliplatin, cetuximab, bevacizumab, panitumumab, ziv-aflibercept, regorafenib, ramucirumab or any combination thereof, for the treatment of colon cancer.

In another particular embodiment of the first aspect of the invention, the G-CSF or GM-CSF is administered separately, simultaneously or sequentially together with a compound selected from the group consisting of 5-fluorouracyl, capecitabine, leucovorin, irinotecan, oxaliplatin, cetuximab, bevacizumab, panitumumab, ziv-aflibercept, regorafenib, ramucirumab or any combination thereof, for the treatment of colon cancer, and the administration of said compounds is optionally combined with radiotherapy.

Throughout the description and claims the word "comprise" and variations of the word, are not intended to exclude other technical features, additives, components, or steps. Furthermore, the word "comprise" and its variations encompasses the term "consisting of". Additional objects, advantages and features of the invention will become apparent to those skilled in the art upon examination of the description or may be learned by practice of the invention. The following examples are provided by way of illustration, and they are not intended to be limiting of the present invention.

Furthermore, the present invention covers all possible combinations of particular and preferred embodiments described herein.

EXAMPLES

A) Material and Methods
Cell Lines

Human pancreatic adenocarcinoma cell lines, Panc-1 and MiaPaca cells and the mouse pancreatic adenocarcinoma cells Panc02, were used for pancreatic cancer efficacy studies. Murine colorectal carcinoma cell line, Colon-26 cells, was used for colon cancer efficacy studies. All cell lines were routinely cultured in Dulbecco's modified Eagle's medium (DMEM) (Lonza, Verviers, Belgium) medium supplemented with 10% Fetal Bovine Serum (FBS), 100 units penicillin/ml, 100 µg streptomycin/ml, and an additional 2 mM glutamine (Lonza), and were kept in a humidified incubator at 37° C., 5% CO2 and passed every 3-4 days.

Mouse Models and Tumor Growth Studies Animal procedures met the guidelines of European Community Directive 86/609/EEC and were approved by the Local Ethical Committee. Female athymic nu/nu mice (6 weeks old, Harlan *Iberica*) were used to generate subcutaneous (SC) pancreatic tumors from Panc-1 and MiaPaca cell lines. Immunocompetent models, C57BJL6 female mice (6 weeks old, Harlan *Iberica*) and Balb/C (6 weeks old, Harlan *Iberica*) were used to generate SC tumors from Panc01 and Colon-26 cell lines, respectively. All cell lines were injected in the right side flank of mice at $6 \times 10^6$/cell/mice. All animals were weighed and tumors were measured using manual caliper three times per week. SC tumor volumes were calculated according to the formula described by Attia and Weiss (Attia M A, et. al. "Immunology of spontaneous mammary carcinomas in mice. V. Acquired tumor resistance and enhancement in strain A mice infected with mammary tumor virus" Cancer Res. 1966, vol. 26, pp, 1787-1800), V (mm$^3$)=0.4×(larger diameter×smaller diameter$^2$).

Antitumoral Efficacy Studies in Pancreatic Cancer Models

To evaluate the antitumoral capacity of G-CSF in different pancreatic cancer models in immunodeficient and immunocompetent mice, treatments were initiated when SC tumors reached a tumor volume ranging from 90 to 110 mm$^3$. For G-CSF therapy, athymic nu/nu mice with Panc-1 (FIG. 1) and MiaPaca (FIG. 2) and C57BJL6 mice with Panc02 (FIG. 3) were randomly divided in Saline, G-CSF (Filgrastim—Amgen) and Gemcitabine (GE) groups. G-CSF treatment was applied subcutaneously every day during the whole experiment, while GE treatment was applied intraperitoneal two times per week during the whole experiment. Details about each treatment are described in the present table:

|  | Doses Administered | |
| --- | --- | --- |
| Cell Lines | G-CSF (µg/Kg) | GE (mg/Kg) |
| MiaPaca | 10 | 80 |
| Panc-1 | 10 | 80 |
| Panc02 | 100 | |

Antitumoral Efficacy Studies in Colon Cancer Model

To evaluate the antitumoral capacity of G-CSF in murine colorectal carcinoma, immunocompetent Balb/C mice bearing Colon-26 tumors were treated when SC tumors reached a tumor volume ranging from 90 to 110 mm$^3$. For G-CSF therapy, Balb/C mice were randomly divided in Saline and G-CSF groups. G-CSF treatment (Filgrastim—Amgen) was applied subcutaneously every day during the whole experiment (FIG. 4). At day 5 of the experiments, 4 animals of each treatment were sacrificed and tumors were collected. Granulocytes (GRA) cells were detected by FACS, analyzing the markers of these cells: CD45+CD11b+Ly6G (FIG. 5). Details about each treatment are described in the present table:

| Cell Lines | Doses Administered G-CSF (µg/Kg) |
|---|---|
| Colon-26 | 10 |

Antitumoral studies were performed as described and animals were sacrificed according to the analysis of signs and symptoms of animal welfare dictated by local ethical guidelines for oncological experimentation studies.
Effects of Sephadex in Colon-26 Model Antitumoral experiments were carried out on immunocompetent Balb/C tumor-bearing mice treated with Sephadex. Sephadex treatments were initiated when SC Colon-26 tumors reached a tumor volume ranging from 90 to 110 mm$^3$ and 0.5 mL of Sephadex 16% (Sephadex G-150, Pharmacia Fine Chemicals, Sweden) was subcutaneously injected in the left side flank of mice. Control animals included were Saline and Sephadex groups. In this experiment, G-CSF group was treated at a dose of 50 µg/Kg (Filgrastim—Amgen). There were 4 animals per group and their survival was monitored daily (FIG. 6). In this model, Sephadex distracts functional granulocytes from the blood into the Sephadex papula thus abolishing G-CSF antitumoral activity.
Assessment of the Peripheral Blood Hemogram As peripheral blood is the only tissue routinely available from mice, the peripheral blood hemogram was also assessed in order to provide information about the behavior of blood cell populations after the subcutaneous injection of different G-CSF doses (Filgrastim—Amgen). The peripheral blood collected from the right femoral artery with a heparinized syringe in vacutainer blood collection tubes containing EDTA (Sarstedt Microvette® CB 300) were immediately subjected to differential blood cell counts (red blood cells (RBCs), white blood cells (WBCs), and blood platelets (PLTs)) and measurement of blood hemoglobin concentration using a blood cell differential automatic analyzer (ABACUS JUNIOR VET). The data for each experimental group were obtained from three to five mice. Inventors especially focused their attention on the distribution of granulocytes in the peripheral blood which was determined at 1, 5 or 2, 6, 10 and 24 hrs after an initial dose of G-CSF subcutaneously. Peripheral blood granulocytes levels were analyzed in healthy (FIG. 7), and tumor-bearing mice (FIG. 8). C57BJL6 healthy mice were injected with G-CSF 10 µg/kg and healthy athymic nu/nu mice were injected with different doses of G-CSF: 0, 10, 25, 50 and 100 µg/kg (FIG. 7). Athymic nu/nu mice bearing subcutaneous MiaPaca tumor were injected with G-CSF 10, 25, 50 and 100 µg/kg and blood was extracted at 1.5 hr (FIG. 8).
B) Results The anti-tumoral effects for colon and pancreatic cancer of the human colony stimulating factors were experimentally verified in a series of in vivo tests (G-CSF).

Before evaluating the antitumoral effect of G-CSF, inventors analyzed the effect of G-CSF on peripheral blood granulocyte levels in healthy immunocompetent and immunodeficient mice. After a single injection of varying doses of G-CSF (10, 25, 50 and 100 µg/Kg) in healthy animals, inventors observed a significant increase of peripheral blood granulocytes in both animal models, reaching maximum levels at 6 hs post-G-CSF injection. The increase of granulocyte levels at the 10 µg/Kg dose in C57BJL6 mice was 2.5-fold compared to untreated animals. On the other hand, the increase of granulocyte levels in Athymic nu/nu mice was similar to C57BJL6 mice. At a dose of 10 µg/Kg of G-CSF the increase of granulocyte levels was 2.5-fold compared to untreated animals, whereas increases for 25, 50 and 100 µg/Kg doses were 3.5-, 3.7- and 3.5-fold, respectively (FIG. 7), confirming that the biological saturated levels were reached with doses higher than 25 µg/Kg.

Figure 1:
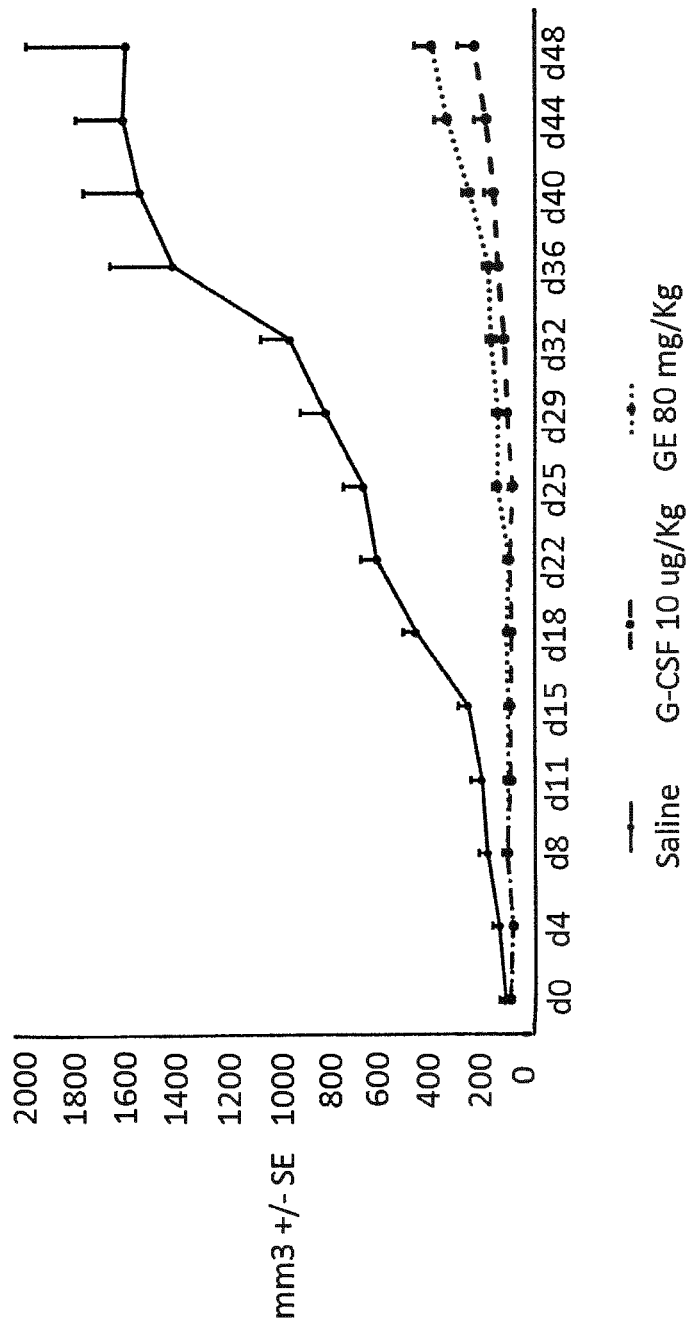
FIG. 1. G-CSF antitumoral efficacy in Panc-1 model.

To assess the antitumor activity of G-CSF (Filgrastim—Amgen), inventors utilized three pancreatic tumor models studies: xenografts from Panc-1, MiaPaca and Panc02 cells for which tumor progression was analyzed by measuring tumor volume. Animals from Panc-1 model were subcutaneously injected with daily doses of 10 µg/Kg of G-CSF and twice a week with 80 mg/Kg of Gemcitabine (GE) as a gold standard treatment, during 48 days of treatment. Treatment with G-CSF produced a strong inhibition of tumor growth, reaching up to 90% of tumor inhibition compared to saline, similar results with gemcitabine were obtained (FIG. 1). Moreover, MiaPaca tumors treated under identical conditions as the Panc-1 model showed a significant inhibition in tumor growth (FIG. 2) 37 days after treatment. In this model, the tumor inhibition capacity reached up to 55% compared to saline. In this model, inventors observed an increase in a dose response manner when the peripheral blood granulocyte levels were analyzed after the first subcutaneous injection of G-CSF at 10, 25, 50 and 100 µg/kg (FIG. 8)

Animals from Panc02 model were subcutaneously injected with daily doses of 100 µg/Kg of G-CSF during 20 days of treatment. Treatment with G-CSF produced less antitumoral activity compared to other human pancreatic tumor models (as Panc-1 and MiaPaca) due to the aggressive profile characteristic of this murine tumor model. The inhibition capacity of the treatment reached around 50% of tumor inhibition compared to saline (FIG. 3).

To determine the therapeutic potential of G-CSF in colon cancer, inventors also evaluated the antitumoral activity in a murine colon cancer model. Immunocompetent animals bearing Colon-26 tumors were subcutaneously injected with daily doses of 10 µg/Kg of G-CSF during 18 days of treatment. Treatment with G-CSF reached up to 60% of tumor inhibition (FIG. 4) and up to 70% of tumor inhibition when immunocompetent animals bearing Colon-26 tumors were subcutaneously injected with daily doses of 50 µg/Kg of G-CSF during 19 days (FIG. 6). In order to study the infiltrating immune cells, mainly neutrophils, into the Colon-26 tumors after G-CSF, inventors performed flow cytometry studies where the expression of three antigens CD45, Ly6G and CD11 b was analyzed. In agreement with the antitumoral effect observed in Colon-26 tumors, the subcutaneous injection of G-CSF at 10 µg/Kg showed a significant increase of tumor-infiltrating granulocytes, defined as a CD45+CD11b+Ly6G+ triple positive population, in this model (FIG. 5). Any toxicity evidence was observed mediated by the daily use of G-CSF for long time represented as a weight loss in all the tumor models studied.

In order to demonstrate that the G-CSF effect was mediated by a pro-inflammatory reaction induced by neutrophils, inventors challenged the antitumoral ability of G-CSF in Colon-26 model by injecting a solution of 15% of Sephadex simultaneously. The Sephadex model has been extensively described in the literature as a technique to verify de implication of immune system in a therapeutic response (Jaganjac M., et. al. "The involvement of granulocytes in spontaneous regression of Walker 256 carcinoma" Cancer Lett. 2008, vol. 260, pp. 180-186), stimulating mainly neutrophils. The purpose of this study was to demonstrate, in an indirectly way, that the antitumor effect of G-CSF is mainly governed by the stimulation of the immune system. In fact, inventors administered a single subcutaneous high dose injection of Sephadex, causing a constant focus of inflammation (thereby attracting immune cells, including those which were stimulated after the daily injections of G-CSF). In theory, if the therapeutic effect of G-CSF against tumor growth was in part due to the stimulation of immune cells, then the result would be a loss of antitumor effect for G-CSF treated animals in the presence of Sephadex. Results obtained are in concordance with this theory, demonstrating that immune system stimulation plays a key role when G-CSF is administered (FIG. 6) in cancer therapy. Immunocompetent animals bearing Colon-26 tumors treated with daily doses of 50 µg/Kg of G-CSF during 19 days, the tumor inhibition reached 70%, while the Immunocompetent animals bearing Colon-26 tumors and Sephadex and treated with daily doses of 50 µg/Kg of G-CSF during 19 days, the tumor inhibition reached 50%, Furthermore, the subcutaneous injection of Sephadex induced lower neutrophils levels in pheripheral blood, which are smoothly recovered after the G-CSF injection.

In summary, these results indicate that daily subcutaneous delivery of G-CSF induces strong antitumoral effects to pancreatic and colon tumors mediated by the specific recruitment of granulocytes to the tumor in these models.

REFERENCES CITED IN THE APPLICATION

Attia M A, Weiss D W. "Immmunology of spontaneous mammary carcinomas in mice. V. Acquired tumor resistance and enhancement in strain A mice infected with mammary tumor virus" Cancer Res. 1966, vol. 26, pp. 1787-1800.
DiMasi J A, Grabowski H G. "Economics of new oncology drug development" J. Clin. Oncol. 2007, vol. 25, pp. 209-216
Spitler L E., et. al. "Adjuvant therapy of stage III and IV malignant melanoma using granylocyte-macrophage colony-simulating factor" J. Clin. Oncol. 2000, vol. 18, pp. 1614-1621
Rini B I, et. al. "Clinical and immunological characteristics of patients with serologic progression of prostate cancer achieving long-term disease control with granulocyte-macrophage colony-stimulating factor" J. Urol. 2006, vol. 175, pp. 2087-2091
Carson E J., et. al. "Phase II trial of sargramostim (yeast-derived recombinant human GM-CSF) as monotherapy for advanced sarcomas" Proc. Am. Soc. Clin. Oncol. 2000, vol 18, Abstract 2219
Demirci, U., et. al. "Serum granulocyte macrophage-colony stimulating factor: a tumor marker in colorectal carcinoma?, Asian Pac. J. Cancer Prev. 2009, vol. 10, pp. 1021-1024
Fujiwara Y. et. al. "Granulocyte colony-stimulating factor-producing ascending colon cancer as indicated by histopathological findings: report of a case." Osaka City Med. J. 2011, vol. 57, pp. 79-84
Jaganjac M., et. al. "The involvement of granulocytes in spontaneous regression of Walker 256 carcinoma" Cancer Lett. 2008, vol. 260, pp. 180-186
Mroczko B. et. al. "Serum macrophage-colony stimulating factor levels in colorectal cancer patients correlate with lymph node metastasis and poor prognosis" Clin Chim Acta. 2007, vol. 380, pp. 208-12.
Kim J S. et. al. "Administration of granulocyte colony-stimulating factor with radiotherapy promotes tumor growth by stimulating vascularization in tumor-bearing mice" Oncol Rep. 2015, vol. 34, pp. 147-54
Morris K T. et. al. "G-CSF and G-CSFR are highly expressed in human gastric and colon cancers and promote carcinoma cell proliferation and migration" Br. J. Cancer 2014, vol. 110, pp. 1211-20
Groblewska M. et. al. "Serum levels of granulocyte colony-stimulating factor (G-CSF) and macrophage colony-stimulating factor (M-CSF) in pancreatic cancer patients" Clin. Chem. Lab. Med. 2007, vol. 45, pp. 30-4.
Joshita S. et. al. "Granulocyte-colony stimulating factor-producing pancreatic adenosquamous carcinoma showing aggressive clinical course" Intern. Med. 2009, vol. 48, pp. 687-91

The invention claimed is:

1. A method of treatment of colon or pancreatic cancer through an increase in neutrophilia, said method comprising administering to a patient in need thereof a therapeutically effective amount of a Colony Stimulating Factor (CSF) as an active ingredient, wherein the Colony Stimulating Factor is selected from the group consisting of Granulocyte Macrophage Colony Stimulating Factor (GM-CSF) and Granulocyte Colony Stimulating Factor (G-CSF); and wherein the CSF is an isolated soluble CSF protein administered as the sole active ingredient.

2. The method of claim 1, wherein the administration of the CSF is by injection.

3. The method of claim 1, wherein the colon cancer is adenocarcinoma of the colon.

4. The method of claim 1, wherein the pancreatic cancer is exocrine pancreatic cancer.

5. The method of claim 1, wherein the Colony Stimulating Factor is Granulocyte Macrophage Colony Stimulating Factor (GM-CSF).

6. The method of claim 5, wherein the GM-CSF is Sargramostim or Molgramostim.

7. The method of claim 1, wherein the Colony Stimulating Factor is Granulocyte Colony Stimulating Factor (G-CSF).

8. The method of claim 7, wherein the G-CSF is Filgrastim, Pegfilgrastim, Lenograstim or Lipegfilgrastim.

9. The method of claim 1, wherein the administration of the CSF is at a dose of between 100 and 1000 µg/day.

10. The method of claim 1, wherein the administered doses are given over a period of between 4 and 16 weeks.

11. The method of claim 1, wherein the administration is subcutaneous, oral, intramuscular or intravenous.

12. The method of claim 1, wherein the administration is at a dose of between 100 and 600 µg/day for G-CSF and at a dose of between 200-800 µg/day for GM-CSF for a period of between 4 and 16 weeks, subcutaneously.

13. The method of claim 1, wherein the induced neutrophilia has a neutrophil count from 15,000 to 45,000 units/ microliter.

14. The method of claim 1, wherein the G-CSF or GM-CSF is administered as a combination chemical antineoplastic therapy.

15. The method of claim 1, wherein G-CSF or GM-CSF is administered separately or sequentially with one or more compounds selected from the group consisting of gemcitabine, paclitaxel, 5-fluorouracyl, leucovorin, irinotecan, oxaliplatin, erlotinib, everolimus, mitomycin C, and sunitinib, for the treatment of pancreatic cancer, and the administration of said compounds is optionally combined with radiotherapy.

16. The method of claim 1, wherein G-CSF or GM-CSF is administered separately or sequentially with one or more compounds selected from the group consisting of 5-fluorouracyl, capecitabine, leucovorin, irinotecan, oxaliplatin, cetuximab, bevacizumab, panitumumab, ziv-aflibercept, regorafenib, and ramucirumab, for the treatment of colon cancer, and the administration of said compounds is optionally combined with radiotherapy.

17. The method of claim 1,
which is for the treatment of pancreatic cancer, the Colony Stimulating Factor being a soluble Colony Stimulating Factor protein which is administered separately with one or more a compounds selected from the group consisting of gemcitabine, paclitaxel, 5-fluorouracyl, leucovorin, irinotecan, oxaliplatin, erlotinib, everolimus, mitomycin C, and sunitinib and the administration of said compounds being optionally combined with radiotherapy; or alternatively
which is for the treatment of colon cancer, the Colony Stimulating Factor being a soluble Colony Stimulating Factor protein which is administered separately with one or more compounds selected from the group consisting of 5-fluorouracyl, capecitabine, leucovorin, irinotecan, oxaliplatin, cetuximab, bevacizumab, panitumumab, ziv-aflibercept, regorafenib, and ramucirumab, and the administration of said compounds is optionally combined with radiotherapy.

* * * * *